US010443527B2

(12) United States Patent
Bumberger et al.

(10) Patent No.: US 10,443,527 B2
(45) Date of Patent: Oct. 15, 2019

(54) EXHAUST GAS SYSTEM WITH A GAS SENSOR, IN PARTICULAR WITH A PARTICLE SENSOR

(71) Applicant: Bayerische Motoren Werke Aktiengesellschaft, Munich (DE)

(72) Inventors: Gerwin Bumberger, St. Ulrich (AT); Gerhard Hofer, Kleinreifling (AT)

(73) Assignee: Bayerische Motoren Werke Aktiengesellschaft, Munich (DE)

( * ) Notice: Subject to any disclaimer, the term of this patent is extended or adjusted under 35 U.S.C. 154(b) by 0 days.

(21) Appl. No.: 15/681,649

(22) Filed: Aug. 21, 2017

(65) Prior Publication Data

US 2017/0370315 A1 Dec. 28, 2017

Related U.S. Application Data

(63) Continuation of application No. PCT/EP2016/060364, filed on May 10, 2016.

(30) Foreign Application Priority Data

May 21, 2015 (DE) .......................... 10 2015 209 262

(51) Int. Cl.
*F02D 41/14* (2006.01)
*F01N 13/00* (2010.01)
*G01N 15/02* (2006.01)

(52) U.S. Cl.
CPC ....... *F02D 41/1466* (2013.01); *F01N 13/008* (2013.01); *F02D 41/1439* (2013.01);
(Continued)

(58) Field of Classification Search
CPC ............. F02D 41/1466; F02D 41/1439; F02D 41/1445; G01N 15/0272; F01N 13/008; F01N 2560/05
See application file for complete search history.

(56) References Cited

U.S. PATENT DOCUMENTS 5,739,414 A * 4/1998 Paulus ................... G01N 27/12
73/23.31
2002/0148279 A1* 10/2002 Weyl ..................... F01N 13/008
73/31.05
(Continued)

FOREIGN PATENT DOCUMENTS

CN           101779015 A      7/2010
DE    10 2008 041 038 A1     2/2010
(Continued)

OTHER PUBLICATIONS

German-language Office Action issued in counterpart German Application No. 10 2015 209 262.3 dated Jan. 21, 2016 (6 pages).
(Continued)

*Primary Examiner* — Joseph J Dallo
(74) *Attorney, Agent, or Firm* — Crowell & Moring LLP

(57) ABSTRACT

An exhaust gas system includes an exhaust gas pipe through which exhaust gas flows in a flow direction and which has a pipe wall. A flange is arranged in the pipe wall and has a passage opening provided with an internal thread. A gas sensor, in particular a particle sensor, is provided for sensing the concentration of soot particles contained in the exhaust gas and has a threaded housing portion that is provided with an external thread and is screwed into the passage opening. An annular gap is produced between a radial outer face of the threaded housing portion and a passage-opening inner circumferential portion which protrudes into the interior of the exhaust gas pipe. The flange has a flow guiding element which extends over a downstream part of the circumference of the threaded housing portion and which is provided for limiting or largely preventing a flow around the gas sensor in the annular gap.

19 Claims, 2 Drawing Sheets

(52) U.S. Cl.
CPC ..... *F02D 41/1445* (2013.01); *G01N 15/0272* (2013.01); *F01N 2560/05* (2013.01)

(56) References Cited

U.S. PATENT DOCUMENTS

| | | | | |
|---|---|---|---|---|
| 2003/0188568 | A1* | 10/2003 | Kurachi | G01N 27/4074 73/31.05 |
| 2007/0056353 | A1* | 3/2007 | Weyl | G01N 27/4077 73/23.31 |
| 2010/0064663 | A1 | 3/2010 | Goya | |
| 2010/0158758 | A1* | 6/2010 | Gustin | F01N 13/008 422/83 |
| 2011/0126610 | A1* | 6/2011 | Sekiya | G01N 27/4077 73/25.05 |
| 2011/0232268 | A1* | 9/2011 | Nelson | G01N 15/0656 60/276 |
| 2012/0085146 | A1 | 4/2012 | Maeda et al. | |

FOREIGN PATENT DOCUMENTS

| | | | | |
|---|---|---|---|---|
| DE | 102008041038 A1 * | 2/2010 | | G01N 27/4074 |
| DE | 10 2011 083 339 A1 | 5/2012 | | |
| JP | 10-293113 A | 11/1998 | | |
| JP | 2012-220109 A | 11/2012 | | |
| JP | 2012220190 A | * 11/2012 | | |
| WO | WO 2004/109270 A1 | 12/2004 | | |
| WO | WO 2012/162685 A1 | 11/2012 | | |

OTHER PUBLICATIONS

International Search Report (PCT/ISA/210) issued in PCT Application No. PCT/EP2016/060364 dated Jul. 14, 2016 with English translation (7 pages).
German-language Written Opinion (PCT/ISA/237) issued in PCT Application No. PCT/EP2016/060364 dated Jul. 14, 2016 (6 pages).
German-language European Office Action issued in counterpart European Application No. 16 721 179.6 dated Sep. 24, 2018 (four pages).
Chinese-language Office Action issued in counterpart Chinese Application No. 201680007642.1 dated Dec. 13, 2018 with English translation (17 pages).

* cited by examiner

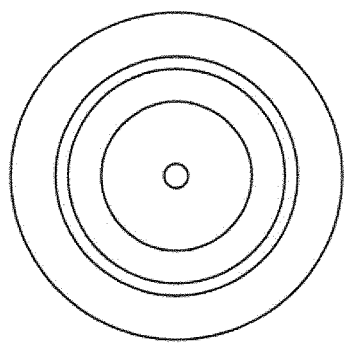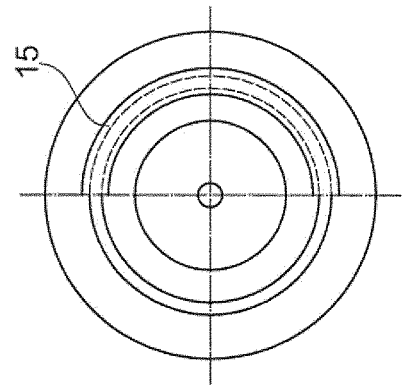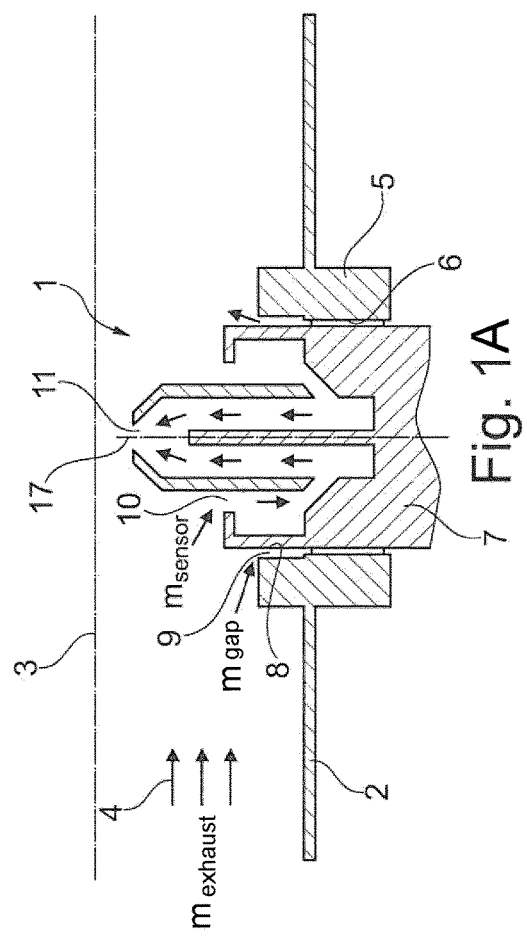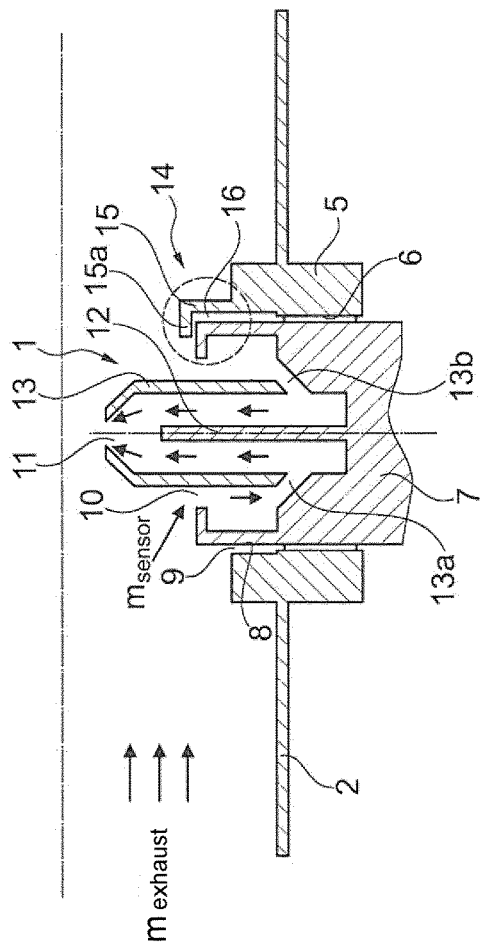

EXHAUST GAS SYSTEM WITH A GAS SENSOR, IN PARTICULAR WITH A PARTICLE SENSOR

CROSS REFERENCE TO RELATED APPLICATIONS

This application is a continuation of PCT International Application No. PCT/EP2016/060364, filed May 10, 2016, which claims priority under 35 U.S.C. § 119 from German Patent Application No. 10 2015 209 262.3, filed May 21, 2015, the entire disclosures of which are herein expressly incorporated by reference.

BACKGROUND AND SUMMARY OF THE INVENTION

The present invention relates to an exhaust gas system with a gas sensor, in particular with a particle sensor.

In order to be able to sense the concentration of soot in the exhaust gas of vehicles having internal-combustion engines, particle sensors are used which are arranged in a pipe element (exhaust gas pipe) of an exhaust gas system.

Company-internally, BMW examined the flow conditions at a particle sensor arranged in an exhaust gas pipe of an exhaust gas system. The examined sensor arrangement is schematically illustrated in FIGS. 1A, 1B.

FIG. 1A shows a gas sensor or particle sensor, which projects into the interior of an exhaust gas pipe 2 having a center longitudinal axis 3. In the exhaust gas pipe 2, an exhaust gas volume flow $m_{exhaustgas}$ flows in a flow direction 4. A flange 5 is arranged in the wall of the exhaust gas pipe 2. The flange 5 has a passage opening provided with an internal thread 6. The gas sensor or particle sensor 1 has a housing 7, which has a threaded housing portion 8 provided with an external thread and screwed into the passage opening or into the internal thread 6 of the flange 5.

As illustrated in FIG. 1A, an annular gap 9 is provided between a radial exterior side of a forward section of the threaded housing portion 8 and an interior circumferential section of the passage opening projecting into the interior of the exhaust gas pipe 2, which passage opening is provided in the flange 5.

A partial volume flow (gap flow) $m_{gap}$ of the exhaust gas volume flow $m_{exhaust}$ can enter into the annular gap 9 and flow around the housing 7 or the threaded housing portion 8 of the particle sensor 1. As a result of the annular gap 9, the flow around the particle sensor is relatively strong, which leads to a drop of the pressure gradient between an exhaust gas input 10 and an exhaust as output 11 of the particle sensor 1. By way of the exhaust gas input 10, a partial volume flow $m_{sensor}$ enters into the particle sensor 1, and, by way of the output 11, exhaust gas flows from the particle sensor 1 back into the exhaust gas pipe.

A good flow through the particle sensor takes place only if the pressure difference between the input 10 and the output 11 is sufficiently high, which is a prerequisite for good measuring results. When this "rinsing gradient" is reduced, a smaller mass flow will flow at a lower local velocity through the particle sensor, whereby less exhaust gas and fewer particles arrive in the sensor, which has an unfavorable effect on the functionality of the sensor.

The present invention begins precisely at this point.

It is an object of the invention to create an exhaust gas system with a gas sensor arranged therein, particularly with a particle sensor arranged therein, which is optimized with respect to the exhaust gas flow conditions such that measuring results can be achieved that are as good as possible. In particular, the flow around the particle sensor, which impairs the rinsing gradient, is to be kept as low as possible.

This and other objects are achieved by an exhaust gas system having an exhaust gas pipe, through which exhaust gas flows in one flow direction, which exhaust gas pipe has a pipe wall. In the pipe wall, a flange is arranged, which has a passage opening provided with an internal thread. A gas sensor is screwed into the passage opening. In particular, the gas sensor may be a soot particle sensor which is provided, for example, for sensing the concentration of soot particles contained in the exhaust gas. The gas sensor has a threaded housing portion provided with an external thread, which threaded housing portion is screwed into the passage opening.

An annular gap (which is required for the purpose of manufacturing) is provided between a radial exterior side of a forward section of the threaded housing portion and an interior circumference section of the passage opening of the flange, which interior circumference section projects into the interior of the exhaust gas pipe.

It is the core of the invention that the flange has a "flow guiding element", which extends along a downstream partial circumference of the threaded housing portion, and which is provided for limiting or largely preventing an exhaust gas flow in the annular gap.

The flow guiding element may be designed similar to "half a fender of a bicycle" or to "half a sleeve". It is the purpose of the flow guiding element to create an "obstacle" for the flow around the particle sensor. By means of the flow guiding element, the flow around the particle sensor is reduced, and the rinsing gradient between an exhaust gas input and an exhaust gas output of the particle sensor is enlarged. As a result of the correspondingly larger pressure gradient, a greater exhaust gas mass flow will occur through the particle sensor, whereby its measuring quality will be improved.

The invention can be constructively implemented in a very simple and cost-effective manner.

According to a further development of the invention, a radial gap is present between the flow guiding element and the downstream partial circumference of the threaded housing portion.

It has been mentioned that the flow guiding element extends over a partial circumference of the threaded housing portion. The partial circumference or circumferential region may, for example, be between 150° and 210°, of the total circumference or between 160° and 200° or between 170° and 190°. The flow guiding element preferably extends over a circumferential area of essentially or exactly 180° of the threaded housing portion.

According to a further development of the invention, the flow guiding element has, in the region of its front-side end, i.e. in the area of its end facing the interior of the exhaust gas pipe, a section projecting radially to the interior toward a center longitudinal axis of the gas sensor or particle sensor. This section, at least to an extent, covers a partial circumference of the front side of the threaded housing portion of the gas sensor or particle sensor.

Between the section of the flow guiding element projecting radially toward the interior and the front side of the threaded housing portion, a space or a small gap may exist—viewed in the direction of a center longitudinal axis of the gas sensor or particle sensor.

The flange, into whose passage opening the gas sensor or particle sensor is screwed, can be welded into the wall of the exhaust gas pipe or can be connected with the exhaust gas pipe in a different fluid-tight manner.

According to a further development of the invention, a partial section of the threaded housing portion of the gas sensor or particle sensor projects by at least a distance beyond a front side of the flange facing the interior of the exhaust gas pipe.

The gas sensor or particle sensor may have a sleeve-type head. The sleeve-type head, in turn, has a center longitudinal axis and projects beyond the flow guiding element in the direction of the interior of the exhaust gas pipe.

The exhaust gas inlet of the gas sensor can be formed by an annular inflow gap or an inflow gap present between the threaded housing portion and the sleeve-type head. By way of this inflow gap, exhaust gas can flow into the housing of the gas sensor.

The sleeve-type head of the gas sensor—viewed in its circumferential direction—has at least one passage, by way of which exhaust gas, which has entered the housing of the gas sensor, can flow farther into the interior of the sleeve-type head.

According to a further development of the invention, the gas sensor has a sensor element, which is arranged in the center in the sleeve-type head or which projects into the sleeve-type head. Exhaust gas entering the sleeve-type head flows along the sensor element to a front-side opening of the sleeve-type head. The front-side opening forms an exhaust gas output of the gas sensor, by way of which exhaust gas flows back into the exhaust gas pipe.

Other objects, advantages and novel features of the present invention will become apparent from the following detailed description of one or more preferred embodiments when considered in conjunction with the accompanying drawings.

BRIEF DESCRIPTION OF THE DRAWINGS

FIGS. 1A, 1B are views of an exhaust gas system having a gas sensor, which was examined internally at BMW and is to be optimized.

FIGS. 2A, 2B are views of an exhaust gas system having a gas sensor according to an embodiment of the invention.

DETAILED DESCRIPTION OF THE DRAWINGS

Figure 3:
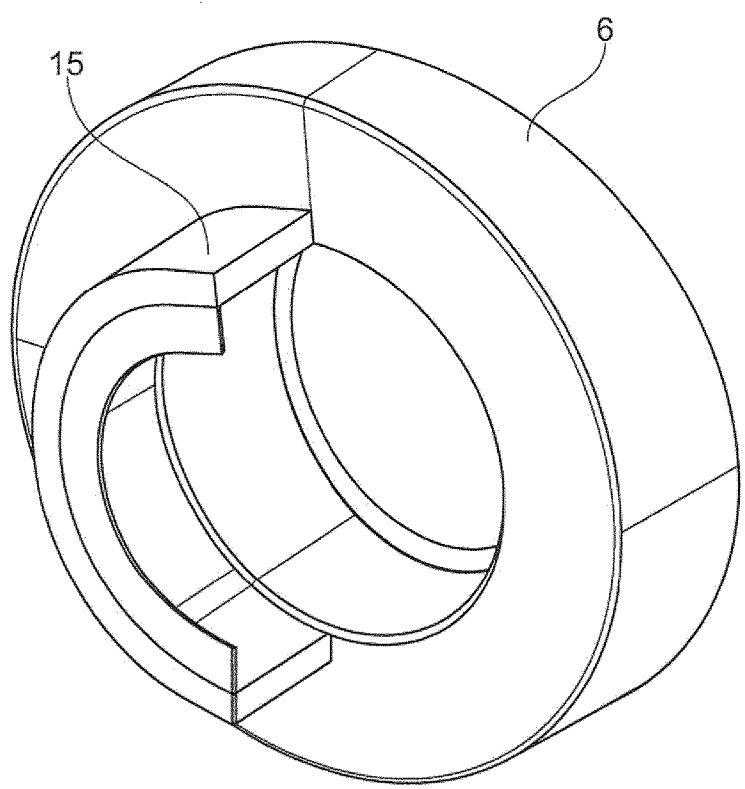
FIG. 3 is a view of a flange according to an embodiment of the invention which has a flow guiding element.

The arrangement illustrated in FIGS. 2A, 2B is largely identical with the arrangement mentioned above in connection with FIGS. 1A, 1B.

A flange 5, which has a passage opening provided with an internal thread 6, is welded into the exhaust gas pipe 2. A soot particle sensor 1 is screwed into the passage opening 6.

The soot particle sensor 1 has a housing 7, which has a threaded housing portion 8. The threaded housing portion 8 is formed by an outer circumference of the housing 7 on which an external thread is provided, which is screwed into the internal-thread 6.

The particle sensor 1 has a sensor element 12, which projects into a sleeve-type head 13 of the gas sensor. An inflow gap exists between the threaded housing section 8 and the sleeve-type head 13, by way of which inflow gap exhaust gas can flow into the gas sensor 1.

The sleeve-type head 13 has several passage openings 13a, 13b, which are distributed in the circumferential direction and, by way of which, exhaust gas flowing into the gas sensor can arrive in the interior of the sleeve-type head.

From there, the exhaust gas flows in the direction of an outflow opening 11, which is provided on a front side of the sleeve-type head 13. By way of the outflow opening 11, exhaust gas flows from the gas sensor 1 back into the interior of the exhaust gas pipe 2.

As illustrated in FIG. 2A, a flow guiding element 15 is arranged in a downstream region 14 of the gas sensor, which flow guiding element 15 extends over a downstream partial circumference of the threaded housing portion 8 (see also FIG. 2B and FIG. 3).

The flow guiding element 15 is provided for limiting or largely preventing an exhaust gas flow in the annular gap 9 and thereby a flow around the particle sensor at its outer circumference or in the annular gap. With respect to its shape, the flow guiding element 15 can be compared with "half a bicycle fender", which is best illustrated in FIG. 3.

As illustrated in FIG. 2A, a radial gap 16 is present between the flow guiding element 15 and a downstream partial circumference of the threaded housing portion 8.

The flow guiding element 15 (similar to a bicycle fender) has a section 15a, which projects radially toward the interior to a center longitudinal axis 17 (see FIG. 1) of the gas sensor 1, which section 15a, at least to an extent, covers a partial circumference of the front side (end face) of the threaded housing portion.

As illustrated in FIGS. 2A, 2B and 3, the flow guiding element 15 here extends over a circumference of 180° of the gas sensor 1.

Between the radially inwardly projecting section 15a of the flow guiding element and the front side of the threaded housing portion 8, there is a small distance or gap—viewed in the direction of a center longitudinal axis 17 (compare FIG. 1) of the gas sensor 1.

A particle filter (not shown) can be arranged in the exhaust gas system. Viewed in the flow direction of the exhaust gas, the gas sensor 1 can be arranged behind the particle filter.

The function of the sensor element 12 is preferably based on a resistance measurement. Soot particles deposited on the sensor element 12 form electrical paths between electrode chambers by way of which a current is flowing. During the operation of the exhaust gas system, the sensor element is regularly regenerated by heating, whereby deposited soot particles are burnt. By means of the measured current, the diagnosis evaluates the functional capacity of the soot particle filter.

In contrast to the arrangement illustrated in FIGS. 1A and 1B, by means of the flow guiding element 15, a flow around the particle sensor or the threaded housing portion 8 is almost completely avoided. The gap volume flow $m_{gap}$ illustrated in FIG. 1A is therefore largely or almost completely prevented, which has a favorable effect on the rinsing gradient and thereby the measuring quality.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. An exhaust gas system, comprising:
   an exhaust gas pipe, through which exhaust gas flows in one flow direction, which exhaust gas pipe has a pipe wall;
   a flange, which is arranged in the pipe wall and which has a passage opening provided with an internal thread;

a gas sensor, which is provided for sensing the exhaust gas, and which has a threaded housing portion provided with an external thread, which threaded housing portion is screwed into the passage opening, wherein an annular gap is provided between a radial exterior side of the threaded housing portion and an interior circumferential section of the passage opening, and the flange has a flow guiding element, which overlaps only a part of a circumference of the threaded housing portion along a longitudinal direction of the exhaust gas pipe, and which is provided for limiting or largely preventing a flow around the gas sensor in the annular gap.

2. The exhaust gas system according to claim 1, wherein a gap is present between the flow guiding element and the downstream partial circumference of the threaded housing portion.

3. The exhaust gas system according to claim 1, wherein the flow guiding element extends over a circumferential region encompassing one of:
    between 150° and 210°,
    between 160° and 200°,
    between 170° and 190°, and
    over essentially or precisely 180°.

4. The exhaust gas system according to claim 2, wherein the flow guiding element extends over a circumferential region encompassing one of:
    between 150° and 210°,
    between 160° and 200°,
    between 170° and 190°, and
    over essentially or precisely 180°.

5. The exhaust gas system according to claim 3, wherein the flow guiding element has a section, which projects radially toward the interior to a center longitudinal axis of the gas sensor, which section, at least to an extent, covers a partial circumference of a front side of the threaded housing portion.

6. The exhaust gas system according to claim 1, wherein the flow guiding element has a section, which projects radially toward the interior to a center longitudinal axis of the gas sensor, which section, at least to an extent, covers a partial circumference of a front side of the threaded housing portion.

7. The exhaust gas system according to claim 5, wherein a space is present between the section of the flow guiding element projecting radially toward the interior and the front side of the threaded housing portion, when viewed in the direction of a center longitudinal axis of the gas sensor.

8. The exhaust gas system according to claim 6, wherein a space is present between the section of the flow guiding element projecting radially toward the interior and the front side of the threaded housing portion, when viewed in the direction of a center longitudinal axis of the gas sensor.

9. The exhaust gas system according to claim 1, wherein the flange is welded into the pipe wall.

10. The exhaust gas system according to claim 1, wherein a partial section of the threaded housing portion projects beyond a front side of the flange facing the interior of the exhaust gas pipe.

11. The exhaust gas system according to claim 1, wherein a sleeve-type head of the gas sensor projects in the direction of its center longitudinal axis beyond the flow guiding element into the interior of the exhaust gas pipe.

12. The exhaust gas system according to claim 1, wherein the gas sensor has an inflow gap between the threaded housing section and the sleeve-type head, by way of which inflow gap exhaust gas flows into the gas sensor.

13. The exhaust gas system according to claim 12, wherein
    a sensor element of the gas sensor projects in the center into the sleeve-type head, gas entering into the sleeve-type head flowing along the sensor element to a front side of the sleeve-type head.

14. The exhaust gas system according to claim 11, wherein
    a sensor element of the gas sensor projects in the center into the sleeve-type head, gas entering into the sleeve-type head flowing along the sensor element to a front side of the sleeve-type head.

15. The exhaust gas system according to claim 13, wherein
    the sleeve-type head has an outflow opening, by way of which exhaust gas flows from the sleeve-type head back into the exhaust gas pipe.

16. The exhaust gas system according to claim 1, further comprising:
    a particle filter, the gas sensor being arranged in the flow direction of the exhaust gas behind the particle filter.

17. The exhaust system according to claim 1, wherein the gas sensor is a particle sensor that senses a concentration of soot particles contained in the exhaust gas.

18. The exhaust system according to claim 1, wherein the flow guiding element directly overlaps the part of the circumference of the threaded housing portion.

19. The exhaust system according to claim 1, wherein the flow guiding element and the part of the circumference of the threaded housing portion extend along the longitudinal direction of the exhaust gas pipe.

* * * * *